United States Patent [19]

Randalls

[11] 4,339,546

[45] Jul. 13, 1982

[54] PRODUCTION OF METHANOL FROM ORGANIC WASTE MATERIAL BY USE OF PLASMA JET

[75] Inventor: Leon C. Randalls, New York, N.Y.

[73] Assignee: Biofuel, Inc., Memphis, Tenn.

[21] Appl. No.: 246,410

[22] Filed: Mar. 23, 1981

Related U.S. Application Data

[63] Continuation-in-part of Ser. No. 121,441, Feb. 13, 1980, abandoned.

[51] Int. Cl.$^3$ .................. C07C 31/04; C07C 27/06
[52] U.S. Cl. .................. 518/704; 518/702; 518/713; 422/186; 422/199; 422/207; 204/170; 435/167; 435/813; 219/121 P; 219/121 PQ; 219/121 PY; 219/121 PB; 252/373
[58] Field of Search .................. 518/702, 704, 713; 422/186, 199, 207; 204/170; 435/167, 813; 219/121 P, 121 PQ, 121 PY, 121 PB

[56] References Cited

U.S. PATENT DOCUMENTS

| | | |
|---|---|---|
| 2,000,224 | 5/1935 | Eisenhul .................. 204/170 |
| 3,663,792 | 5/1972 | Fey. |
| 3,705,975 | 12/1972 | Wolf et al. |
| 4,010,090 | 3/1977 | Fey et al. |
| 4,022,665 | 5/1977 | Ghosh. |
| 4,038,512 | 7/1977 | Wolf et al. |
| 4,067,801 | 1/1978 | Ishida et al. |
| 4,134,830 | 1/1979 | Skogman et al. |

FOREIGN PATENT DOCUMENTS 2398110  3/1979  France .................. 435/167

OTHER PUBLICATIONS

Fey and Read "Arc Heater Pyrolysis of Hydrocarbons" Westinghouse Electric Corp., Jun. 8–12, 1980.
"Chemical Reactions in Plasma Jets", pp. 260–262; 268–274; 279–281.

*Primary Examiner*—Howard T. Mars
*Attorney, Agent, or Firm*—Wood, Herron & Evans

[57] ABSTRACT

Methanol is produced from an organic waste material such as sewage by a process wherein an arc heater or "plasma jet" performs novel process steps including: (1) partially vaporizing an organic sewage sludge (a semi-liquid material produced by bacterial digestion of the sewage); (2) reacting the gas products obtained by the sludge vaporization, together with a digester gas (obtained by digestion of the sewage), to form a synthesis gas comprising principally $H_2$, $CO$, $CO_2$, $H_2O$ and $CH_4$, and (3) optionally, driving a water shift reaction to convert a portion of the output gases to additional $H_2$ and $CO$ for use as a feed stream to the jet. The synthesis gas is converted to methanol in a subsequent process step.

13 Claims, 1 Drawing Figure

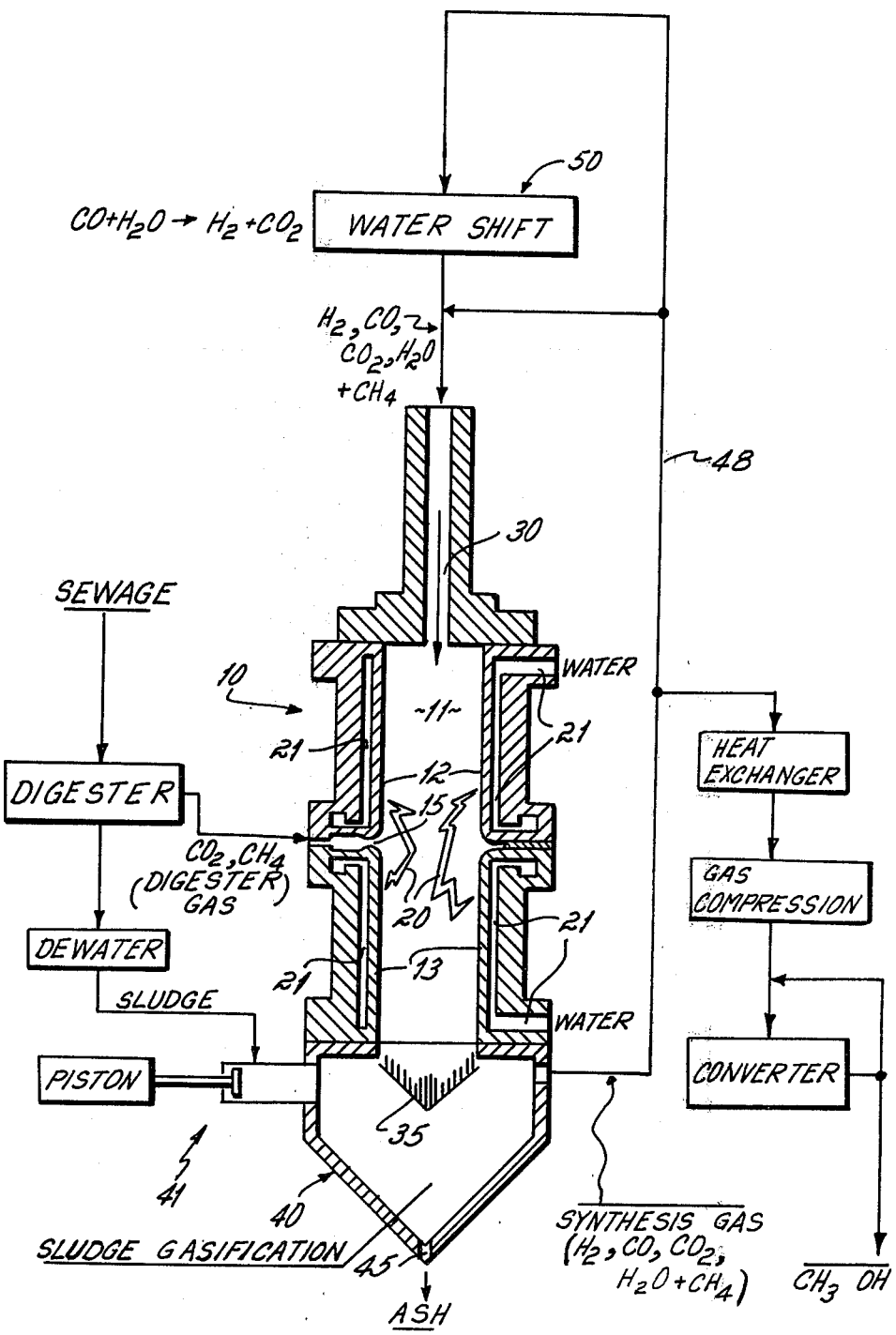

PRODUCTION OF METHANOL FROM ORGANIC WASTE MATERIAL BY USE OF PLASMA JET

RELATED APPLICATION

This application is a continuation-in-part of my co-pending patent application Ser. No. 121,441, filed Feb. 13, 1980, now abandoned, titled "Conversion of Sewage Wastes to Methyl Alcohol."

FIELD OF THE INVENTION

This invention relates to the production of methanol, $CH_3OH$, from digestible material such as sewage.

BACKGROUND

In my above-identified application there is disclosed a method of producing methanol from sewage wastes by bacterially digesting the sewage to form a digester gas continaing $CH_4$ and $CO_2$; next, reforming the digester gas to produce a mixture of $H_2$, CO, $CO_2$ and $CH_4$, and then converting these gases, as by a CuO quench converter, to form methanol. The disclosure of that application is incorporated herein by reference.

BRIEF DESCRIPTION OF THE INVENTION

This invention centers around the discovery that a unique and synergistic effect can be obtained by use of a plasma jet as a reactor/vaporizer in the production of methanol from organic wastes. In accordance with this invention, a plasma jet (sometimes referred to in the art as an "arc heater") converts or reforms liquid and gaseous products obtained by digestion of the organic material, into gaseous reaction products which are then converted to methanol.

The plasma jet is well known per se. Essentially it is a form of ultra-high temperature heat exchanger, wherein a high current electric-arc discharge between electrodes acts upon a process gas stream that passes through the arc and is pyrolyzed as it comes into contact with the arc. These devices are commercially available, one suitable device being marketed by Westinghouse Electric Corporation under their mark "Marc 31." The arc may rotate at high speed to promote uniform heating of the stream and to prevent electrode damage. Reference may be had to Fey U.S. Pat. No. 3,663,792, issued May 16, 1972, titled "Apparatus and Method of Increasing Arc Voltage and Gas Enthalpy in a Self-Stabilizing Arc Heater"; Wolf et al U.S. Pat. No. 3,705,975, issued Dec. 12, 1972, titled "Self-Stabilizing Arc Heater Apparatus"; and to Fey, M. G., and Reed, W. H., "Arc Heater Pyrolysis of Hydrocarbons," Westinghouse Electric Corporation, presented at AIChE National Meeting, 1980, wherein the construction and operation of plasma jets are further described.

Plasma jets produce gas temperatures up to 6000° F. or even more. They have been used for preparation of metal oxides, metals of extremely fine particle size, and hyperheating of gases. They have been used for solid reactions using coal to yield acetylene; the preparation of cyanogen (CN) from graphite and nitrogen; and the preparation of HCN from the reaction of solid carbon with $H_2$ and $N_2$ gases, see Fey et al U.S. Pat. No. 4,010,090, issued Mar. 1, 1977, titled "Process for Converting Naturally Occurring Hydrocarbon Fuels into Gaseous Products by an Arc Heater"; *Techniques and Application of Plasma Chemistry*, Hollahan, John, London Press, 1974; and *Plasma Engineering*, Kettani, M. A., N.Y. Press, 1973.

So far as I am aware, it has not previously been proposed to utilize a plasma jet to carry out the reaction of a digester gas to form a gas suitable for conversion to methanol, or to vaporize digested sludge to a gas suitable for conversion to methanol.

In this invention, sewage or other organic waste is first digested bacterially to produce a digester gas comprising a mixture principally of $CO_2$ and $CH_4$, and a sludge. The digester gas is fed into the arc of the jet and is converted to a mixture of $H_2$, CO, and a small proportion of $CO_2$. These gases, superheated by the jet, are applied to heat the sludge to a pyrolyzing temperature, and thereby gasify it. This produces additional quantities of $H_2$, CO, $CO_2$, $H_2O$, $CH_4$, and a small proportion of other gases such as $H_2S$. At least some of these are supplied back to the jet. Optionally, the jet can also drive a water shift reaction to produce additional hydrogen and carbon dicxide as feed to the jet. The gases from the jet output and the gasified sludge are converted to methanol, as by CuO conversion.

In this process the gasification of the digester sludge provides two highly desirable results. The sludge, in large volume, can present a major disposal problem. By the gasification, the sludge solids are reduced to an ash which has only a small volume in comparison to the sludge (e.g., about 20% ) so that the solids disposal problem is reduced to minimal proportions.

Secondly, and surprisingly, the gaseous products produced by sludge gasification are themselves of utility for the operation of the plasma jet, and for conversion to methanol.

BRIEF DESCRIPTION OF THE DRAWING

The drawing is a schematic flow diagram of a method in accordance with a preferred embodiment of the invention, for converting sewage into methanol, and for gasifying the digester sludge.

DETAILED DESCRIPTION OF THE INVENTION

In the production of methanol from sewage in accordance with this invention, the first step is the digestion of the sewage to produce digester gas and a sewage sludge. This step is well known in the art and may be carried out by conventional means. Commonly this involves screening, settling, mixing, and bacterial digestion.

By way of example, in one common sewage digesting technique the incoming raw sewage is screened on a screen of one inch mesh to remove sticks, stones, and other coarse materials. The throughput of the screen flows to a grit chamber, wherein fine solids such as sand settle to the bottom and are removd as by a worm conveyor. The grit may be used for landfill or combustion. From the grit chamber the organic-containing effluent is pumped or flows to a settling tank. There the organics settle to the bottom of the tank to form a sludge. The sludge is delivered to a mixing tank where it is mixed to a desired water/solids ratio, for example about 5-8% solids. Coal may be added to increase the solids, e.g., at a ratio such that coal comprises about 10-40% of the total sludge solids. The organic sludge is then pumpted to a digester tank.

The digestion itself may be carried out by aerobic or anaerobic bacteria. Digestion produces a mixture of gases containing principally $CO_2$ and $CH_4$. The gas mixture produced by the digestion is referred to herein as "digester gas." Although the methane is, of course, combustible, because the proportion of methane in the digester gas is low, such gas is a low grade fuel and is not especially useful as such. If the content of the digester gas contains too large a percentage of $CO_2$ (greater than about 24% by volume), the digester gas is desirably scrubbed to reduce its $CO_2$ content.

In addition to digester gas, the digestion also produces a sewage sludge, typically of about 5 to 8% solids. In one common type of digester, about 1 lb. of volatile sludge solids is produced for each 15 cu. ft. of digester gas. Reference may be had to my previously identified copending application for a further description of suitable means for effecting digestion. Reference may also be had to *Bioconversion of Waste Materials*, Noye Data Co., 1972, for a further description of the digestion processes for producing digester gas and sludges. As noted, the digestion process may be conventional and does not comprise the invention.

In accordance with this invention, the $CO_2$— and $CH_4$— containing digester gas is converted to $H_2$, CO, and $CO_2$ by reaction in a plasma jet. The jet intensely heats the digester gas by an arc between electrodes within the jet. The drawing illustrates the use of a Westinghouse "Marc 31" arc heater for this purpose.

As shown, the jet 10, of construction known per se, has a cylindrical arc chamber 11, defined within axially spaced apart, hollow, tubular electrodes, which are shown at 12 and 13. Circumferentially spaced gas injection ports as at 15 are presented between the adjacent ends of electrodes 12 and 13 and the digester gas is there introduced. The electrodes are at high potential (up to 4000 volts at 60 hz.) and an arc jumps the gap between them (about 0.040" gap in the March 31), as indicated diagrammatically at 20. The electrodes are internally cooled by circulating water, as at 21. To promote better uniformity of heating and to reduce electrode burn, the high current arc discharge may be rotated around the axis of the heater by a magnetic field rotating at very high speeds, up to 60,000 rpm, as taught in the arc heater patents previously identified.

The digester gas stream is admitted into the arc space through port 15 between the electrodes and is pyrolyzed by the arc.

A second reactant gas stream is preferably also admitted to the arc chamber 11, as through an upstream axial port 30. The second inlet gas stream preferably comprises a mixture principally of $H_2$ and CO gases (generated as hereinafter described more fully), flows into the arc chamber upstream of arc 20, and is reacted and mixed with the digester gas.

The arc heats the gases very rapidly and they expand to form a "jet" 35 which exits the arc chamber through an open "downstream" end thereof, and are applied to gasify the digested sewage sludge, as will now be described.

The sludge from the digester is preferably first dewatered, to increase its solids content. To the same end, additional solids can be added, for example coal, municipal waste, or even ash; or it may be preheated to drive off water before entering the gasification zone 40. This increases its consistency for ease of handling in subsequent gasification. The sludge is delivered to a gasification chamber 40, wherein it is exposed directly (or indirectly, as by a heat exchanger) to the intense heat (e.g., 1800° F.) of the gases exiting from arc heater 10. A portion of the sludge is thereby gasified. In the preferred embodiment shown, this is done by pumping the sludge to the chamber 40, as by a piston operated reciprocating plunger 41. The ram of the plunger positively displaces and thereby meters the flow of sludge into chamber 40. In an alternative embodiment, the jet exhaust gases are passed through a heat exchanger and compressed to increase pressure to 15 to as much as 1500 psi before sludge gasification.

In the gasification zone the heat of the arc output gases partially volatilizes the sludge. Up to about 70–80 wt.% of the sludge can be volatilized by this procedure. The remainder is an ash which is removed from chamber 40 as by a line 45.

Gasification of the sludge can produce about 15 scf of gas per pound of sludge solids. Because of the water content of the sludge, large quantities of steam are produced. The gases thereby produced mix with the jet output gases in chamber 40 to produce a mixture of principally $H_2$, CO, $CO_2$, $CH_4$ and $H_2O$. Illustratively, their proportions may be about:

| | |
|---|---|
| 27 vol. % | $H_2$ |
| 15 vol. % | CO |
| 12 vol. % | $CO_2$ |
| 16 vol. % | $CH_4$ |
| 28 vol. % | $H_2O$ |
| 2 vol. % | $H_2S$, other |
| 100 | |

These proportions vary with temperature and pressure; the values given are for gasification at 50 psi and 1800° F.

I have found that the gas mixture so produced is eminently suitable for conversion into methanol, as later described.

In general, the plasma jet operates most efficiently for the reactions desired herein, if it is fed with a mixture of $H_2$ and CO. These gases are present in the synthesis gas produced by the sludge gasification, that is, the sludge gasification produces the very products that are useful to enable the plasma to run efficiently to gasify the sludge. For this reason it is preferred to utilize some of the gas produced by the sludge gasification as input gas to the plasma. For example, gas from gasification zone 40 is taken via line 48 to the jet wherein it is introduced axially through the port 30.

The synthesis gas is converted to methanol in accordance with known technology. It is presently preferred to use a so-called "quench converter" using CuO as the catalyst. Such a conversion step is operated for example at about 800° F., at 750 psi, over a CuO catalyst bed. The converter converts about 5–7% of the gases to methyl alcohol, per pass, with recycling. Other types of synthesis gas converters for methyl production are also known in the art and can be used, see for example Cahn et al U.S. Pat. No. 3,993,457, issued Nov. 26, 1975, titled "Concurrent Production of Methanol and Synthetic Natural Gas."

The $CH_3OH$ gas from the converter is condensed and separated from other gases. Unreacted but reactable gases are desirably recycled through the converter to improve yield.

Because of the high temperature of the jet output, a "water shift" reaction occurs between the CO and $H_2O$ gases of the jet output, with resulting production of $H_2$ and $CO_2$. In order to further improve jet efficiency, it is preferred to further enrich the $H_2$ content of the output synthesis gas, and to supply the thus "enriched" synthesis gas to the jet. This can be done, as shown in the drawing, by an optional further water shift stage in the recycle stream, as at 50. The water shift stage, known per se, can for example be operated at 500°–800° F. and 50–1500 psi over a catalyst such as iron oxide, cobalt oxide, or chromia. Alternatively, additional CO and $H_2$ can be generated as "water gas" by decomposing steam over incandescent coke or by high temperature reaction of steam with natural gas or similar hydrocarbons. These improve plasma jet efficiency.

Having described the invention, what is claimed is:

1. The method of producing methanol from organic waste comprising, digesting the waste to produce a digester gas comprising a mixture of $CO_2$ and $CH_4$, and a sludge, supplying said digester gas into the arc of a plasma jet, also supplying $H_2$ and CO gases into said arc, said plasma jet producing a hot output gas stream containing principally $H_2$, CO, and $CO_2$, applying heat from said output gas stream to said sludge to gasify a portion of said sludge, thereby producing a synthesis gas comprising a mixture of $H_2$, CO, $CO_2$, $H_2O$ and $CH_4$ as the major components thereof, and an ash residue, and converting said synthesis gas to methanol.

2. The method of claim 1 further including the steps of, generating additional $H_2$ by the water shift reaction of CO with $H_2O$, and supplying into the plasma jet $H_2$ produced by the water shift reaction.

3. The method of claim 1 wherein said output gas stream impinges on said sludge in a sludge gasification chamber.

4. The method of claim 3 wherein the sludge is dewatered before it is introduced into said gasification chamber.

5. The method of claim 1 wherein the sludge is dewatered by drying before being introduced into said gasification chamber.

6. The method of claim 1 wherein the synthesis gas is converted to methanol by conversion over CuO as a catalyst.

7. The method of claim 1 wherein the synthesis gas is cooled in a heat exchanger, then compressed before its conversion to methanol.

8. The method of claim 1 wherein the digester gas is introduced between tubular axially spaced electrodes in the arc heater.

9. The method of claim 1 wherein the sludge is gasified by indirect heating by the output gas stream, through heat exchange means.

10. The method of claim 1 wherein said organic waste is sewage.

11. The method of claim 1 wherein said waste is bacterially digested.

12. The method of claim 2 wherein said water shift reaction is carried out over a metal oxide catalyst at a temperature above 500° F.

13. The method of claim 1 wherein the $H_2$ and CO supplied into said arc are provided by the output gas stream.

* * * * *